US008286899B2

(12) United States Patent
Schowalter et al.

(10) Patent No.: US 8,286,899 B2
(45) Date of Patent: Oct. 16, 2012

(54) TISSUE DICING AND PARTICLE SEPARATION DEVICE

(75) Inventors: Joseph P. Schowalter, South Lebanon, OH (US); Prasanna Malaviya, Mason, OH (US); David A. Witt, Maineville, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 231 days.

(21) Appl. No.: 12/777,783

(22) Filed: May 11, 2010

(65) Prior Publication Data
US 2011/0282372 A1 Nov. 17, 2011

(51) Int. Cl.
*B02C 19/00* (2006.01)
(52) U.S. Cl. .................... 241/2; 241/282.1; 241/283
(58) Field of Classification Search .............. 241/2, 30, 241/283, 277, 282.1, 282.2
See application file for complete search history.

(56) References Cited

U.S. PATENT DOCUMENTS

| 3,298,411 | A | 1/1967 | Rosett et al. |
| 5,526,822 | A | 6/1996 | Burbank et al. |
| 5,694,951 | A | 12/1997 | Bonutti |
| 6,086,544 | A | 7/2000 | Hibner et al. |
| 6,990,982 | B1 | 1/2006 | Bonutti |
| 7,115,100 | B2 | 10/2006 | McRury et al. |
| 7,442,171 | B2 | 10/2008 | Stephens et al. |
| 7,611,473 | B2 | 11/2009 | Boock et al. |
| 2004/0078090 | A1 | 4/2004 | Binette et al. |
| 2004/0193071 | A1 | 9/2004 | Binette et al. |
| 2005/0038520 | A1 | 2/2005 | Binette et al. |
| 2005/0113736 | A1 | 5/2005 | Orr et al. |
| 2005/0125077 | A1 | 6/2005 | Harmon et al. |
| 2008/0035767 | A1 | 2/2008 | Schmid et al. |
| 2008/0071385 | A1 | 3/2008 | Binette et al. |
| 2008/0214955 | A1 | 9/2008 | Speeg et al. |
| 2008/0234715 | A1 | 9/2008 | Pesce et al. |
| 2008/0285378 | A1 | 11/2008 | Roggero |
| 2008/0311219 | A1 | 12/2008 | Gosiewska et al. |
| 2010/0160819 | A1 | 6/2010 | Parihar et al. |

FOREIGN PATENT DOCUMENTS

| CN | 2218603 | 1/1996 |
| DE | 43 01 787 | 8/1994 |
| GB | 593 274 | 10/1947 |

OTHER PUBLICATIONS

International Search Report and Written Opinion dated Sep. 27, 2011 for Application No. PCT/US2011/035925.

*Primary Examiner* — Mark Rosenbaum
(74) *Attorney, Agent, or Firm* — Frost Brown Todd LLC

(57) ABSTRACT

A tissue dicing and separation device comprises a housing having an interior that receives tissue for dicing and separation. The device includes a blade assembly connected to a motor and solenoid. The solenoid reciprocates the blade assembly while the motor clocks the blade assembly during each reciprocation cycle. This reciprocating and clocking action of the blade assembly dices and/or minces the tissue. The housing is filled with a fluid and then the blade assembly is continuously rotated to create a vortex within the housing. The vortex causes the diced tissue particles to separate by particle size. Outlets at different positions along the housing permit withdrawal of a slurry of fluid and tissue particles with the tissue particles having a desired size range. The obtained slurry may be used in conjunction with a fistula plug treatment device and method.

20 Claims, 10 Drawing Sheets

TISSUE DICING AND PARTICLE SEPARATION DEVICE

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly, point out and distinctly claim the invention, it is believed the present invention will be better understood from the following description of certain examples taken in conjunction with the accompanying drawings. In the drawings, like numerals represent like elements throughout the several views.

Figure 1:
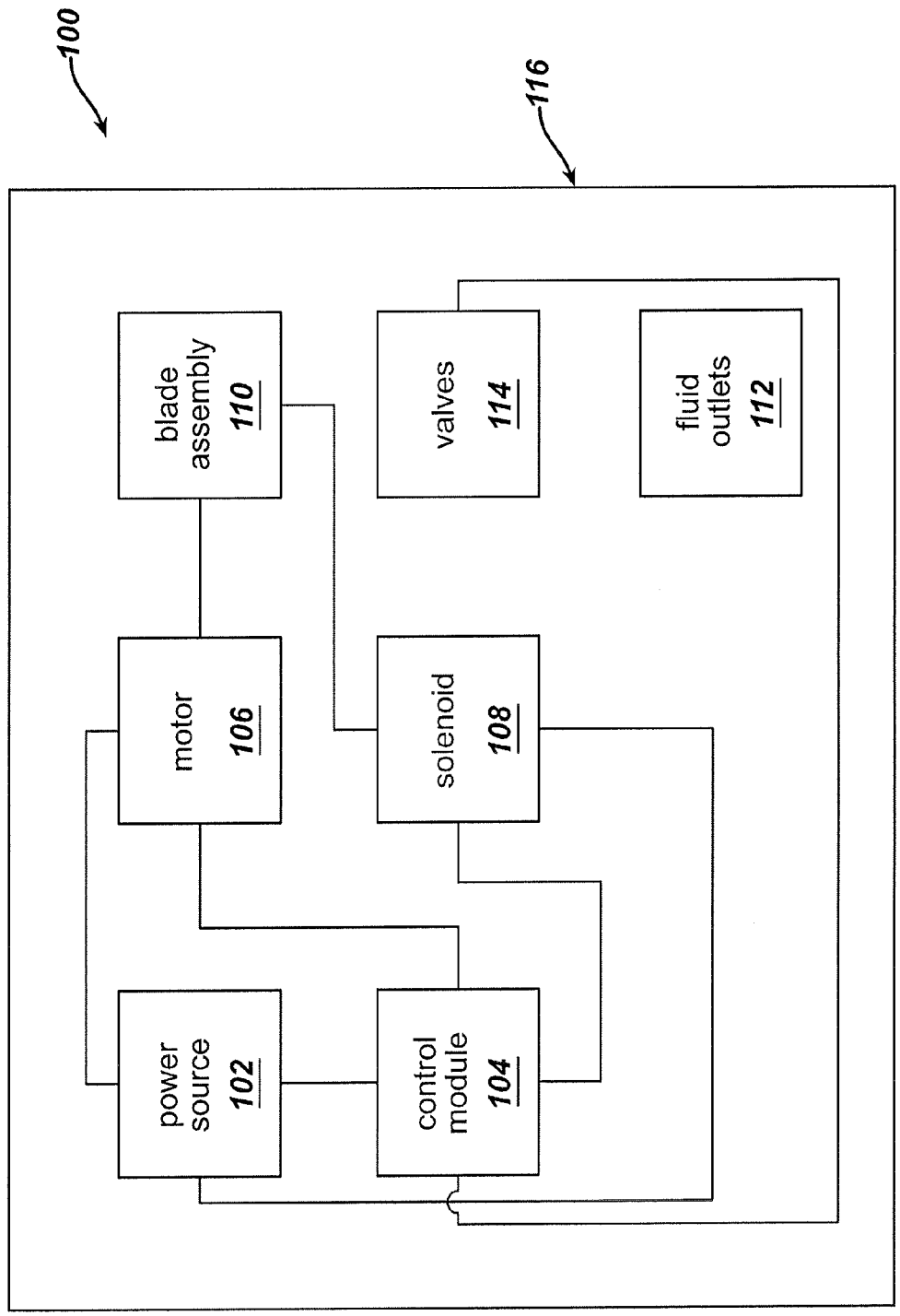
FIG. 1 depicts a system schematic of an exemplary tissue dicing and particle separation device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008; and U.S. Non-Provisional patent application Ser. No. 12/483,305, entitled "Tetherless Biopsy Device with Reusable Portion," filed Jun. 12, 2009. The disclosure of each of the above-cited U.S. patents, U.S. patent application Publications, and U.S. Non-Provisional patent applications is incorporated by reference herein. Such biopsy devices may be used to extract a plurality of tissue specimens from one or more sites in a single patient. It should also be understood that any suitable device described in any other reference that is cited herein may be used to harvest tissue. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly (ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. Merely illustrative examples of how the walls of a fistula may be treated and how a medical fluid may be applied in a fistula will be described in greater detail below. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

In some settings, a single device may be used to mince and mix tissue from a patient to form a medical fluid or later be incorporated in a medical fluid. Another device may be used to administer the medical fluid to the patient. Various examples of devices that may perform at least some of these functions will be described in greater detail below, while other examples will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Tissue Dicing and Particle Separation Device

FIGS. 1-5 depict an exemplary tissue dicing and particle separation device (100), which is operable for use in preparing biological components for application to a treatment site (e.g., a fistula) to promote and improve healing at the site, as discussed above. However, those of ordinary skill in the art will appreciate that tissue dicing and particle separation device (100) may be used for a variety of other purposes. As illustrated in FIG. 1, device (100) of the present example comprises a power source (102), a control module (104), a motor (106), a solenoid (108), a blade assembly (110), fluid outlets (112), valves (114) associated with fluid outlets (112), and a housing (116). These components and their features will be discussed further below.

Power source (102) provides power to control module (104), motor (106), and solenoid (108). Of course in some versions multiple power sources may be used. In some versions, power source (102) is an electric power source. In some other versions, power source (102) is pneumatic or hydraulic. Power source (102) is attached to housing (116) or another component of device (100). Alternatively, power source (102) may be located remote from device (100) and provide power to device (100) by cables, or other power transmission means, connecting device (100) to power source (102). In some versions, power source (102) is a battery while in other versions power source (102) is provided by a connection to a central electrical distribution grid (e.g., via a standard 110 v receptacle). In view of the teachings herein, other features and configurations for power source (102) will be apparent to those of ordinary skill in the art.

Control module (104) provides controlling means for motor (106), solenoid (108), and for valves (114) of fluid outlets (112). Control module (104) of the present example comprises a microprocessor having a control logic in communication with a user interface, that in some versions, comprises two on-off switches that separately control motor (106) and solenoid (108), and one open-close switch to control valves (114). In some versions, valves (114) are configured for independent control such that each valve (114) is operable by its own switch or actuation device. In some versions, control module (114) is coupled with a sophisticated graphical user interface with a touch-screen display. Control module (114) is configured with certain logic to control motor (106), solenoid (108), and valves (114) in a desired fashion. For instance, the logic associated with control module (104) in part relates to synchronized control of motor (106) and solenoid (108) as they relate to blade assembly (110) as will be described in greater detail below. Also in some versions, the logic associated with control module (104) is designed such that certain control features of control module (104) are enabled or disabled depending on the state of device (100). For example, when device (100) is in a partially disassembled state for adding tissue, the logic associated with control module (104) may disable motor (106) and/or solenoid (108) to prevent inadvertent activation when blade assembly (110) may be exposed to a user. In view of the teachings herein, other features and configurations for control module (104) will be apparent to those of ordinary skill in the art.

Motor (106) of the present example comprises an electric motor that converts electricity from power source (102) into mechanical motion. For instance, motor (106) may comprise a DC motor, an AC motor, or some other type of motor. In some other versions, motor (106) comprises a pneumatic motor, a hydraulic motor, or a piezoelectric motor instead. In the present example, motor (106) comprises a conventional stepper motor. Of course, any other suitable motor may be used instead (e.g., induction motors, brushed motors, brushless motors, etc.). As will be discussed in greater detail below, motor (106) provides rotational energy to blade assembly (110). In the illustrated version of FIGS. 2-5, motor (106) is mounted to housing (116) of device (100). However, in some other versions, motor (106) may be located remotely from device (100) and the rotational energy provided by motor (106) is transferred to blade assembly (110) by an intermediate component (e.g., drive shaft, speedometer cable, belt, etc.). Motor (106) may further be associated with a transmission such that rotational speed and torque of blade assembly (110) can be controlled. In view of the teachings herein, other features and configuration for motor (106) will be apparent to those of ordinary skill in the art.

Solenoid (108) of the present example comprises an electromechanical solenoid associated with blade assembly (110). Alternatively, solenoid (108) may comprise a pneumatic linear actuator, a hydraulic linear actuator, a piezoelectric oscillator, an electroactive polymer actuator, an electromagnetic actuator, and/or a variety of other types of movement-inducing devices. As will be discussed in greater detail below, solenoid (108) provides linear energy to blade assembly (110) for reciprocating blade assembly (110). Solenoid (108) of the present example is resiliently biased (e.g., by a spring, etc.) such that blade assembly (110) is biased to a lowered position when solenoid (108) is not energized. When solenoid (108) is energized, the resilient bias is overcome, causing the blade assembly (110) to raise to an upper position. When power to solenoid (108) is interrupted, blade assembly (110) returns to its biased lowered position. Of course, solenoid (108) may instead be resiliently biased to hold blade assembly (110) in an upper position or some other position; or may lack a resilient bias altogether. In the illustrated version of FIGS. 2-5, solenoid (108) is mounted to housing (116) of device (100). However, in some other versions, solenoid (108) may be located remotely from device (100) and the linear energy provided by solenoid (108) transferred to blade assembly (110) by an intermediate component. In view of the teachings herein, other features and configuration for solenoid (108) will be apparent to those of ordinary skill in the art.

Figure 2:
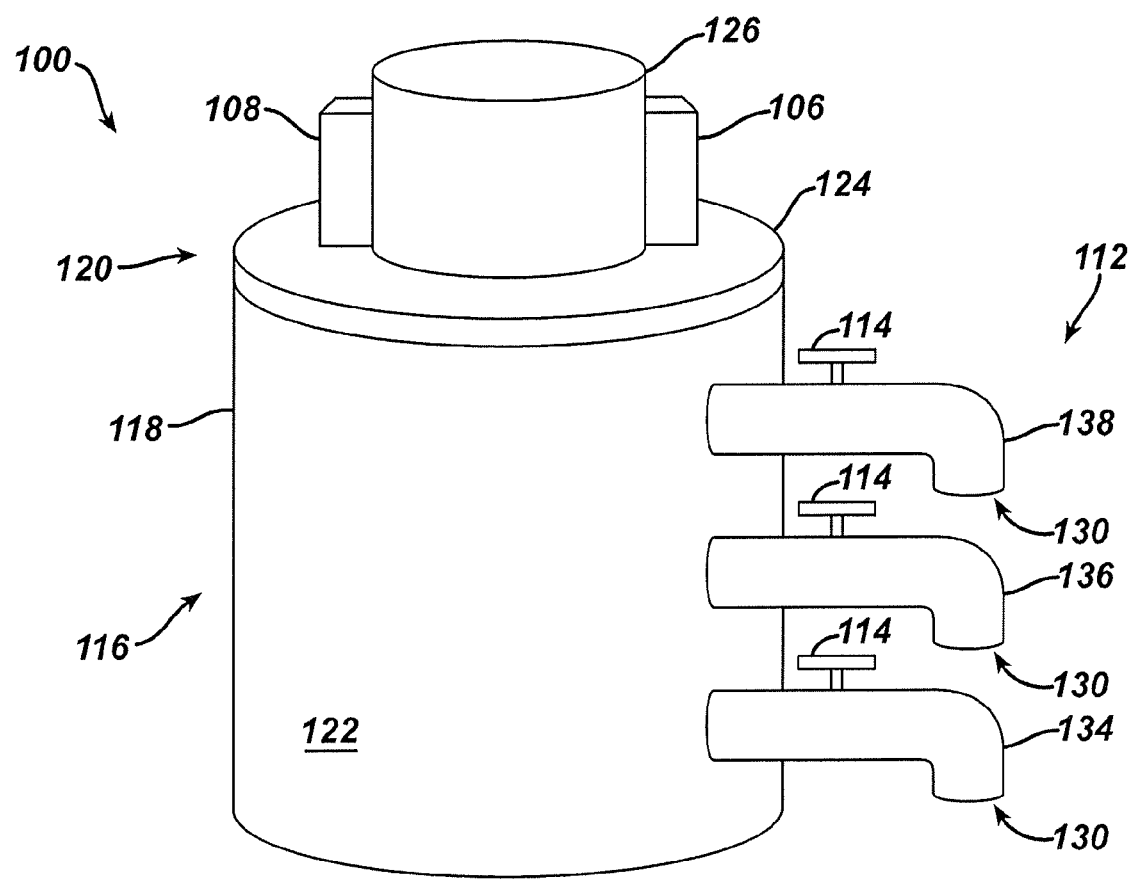
FIG. 2 depicts a perspective view of the device of FIG. 1.

More details regarding blade assembly (110), fluid outlets (112), valves (114), and housing (116) will be discussed below with respect to FIGS. 2-5. Generally though, blade assembly (110) is associated with motor (106) for rotation; and with solenoid (108) for reciprocation as mentioned previously. Blade assembly (110) is configured for use in both dicing and particle separation operations as discussed further below. To the extent that terms such as "dice" and "dicing" are used herein, those terms should not be read as requiring tissue to be cut into cube shapes. It should be understood that dicing tissue may yield tissue portions having various non-cubic shapes in addition to or in lieu of tissue portions having cubic shapes. As best seen in FIG. 2, fluid outlets (112) are integrated components with housing (116) of device (100) and facilitate removal of separated tissue particles from device (100). Valves (114) are included as components of fluid outlets (112) and are configured to control flow from fluid outlets (112). Housing (116) is designed to contain many of the components of device (100) as shown schematically in FIG. 1. For instance, power source (102), control module (104), motor (106), solenoid (108) are all connected with housing (116). Of course, as mentioned above any of these components may be located remotely from housing (116) and indirectly connected with housing (116) or other components of device (100) through various means. Blade assembly (110), fluid outlets (112), and valves (114) are also connected with housing (116) in the present example.

As illustrated in FIG. 2, housing (116) of the present example comprises lower section (118) and upper section (120). Lower section (118) comprises a cylindrical shape (although other shapes could be used) with fluid outlets (112) extending laterally from sidewall (122). Lower section (118) is configured to hold tissue for a subsequent dicing and particle separation procedure. Upper section (120) comprises lid (124) and top (126). Top (126) is connected with lid (124), and lid (124) is configured to be positioned adjacent lower section (118) to selectively seal housing (116). In some versions lid (124) connects with lower section (118) using a threaded configuration. In some other versions lid (124) is fitted with an o-ring and uses a compression-fit with lower section (118). In the illustrated version of FIG. 2, upper section (120) is configured such that blade assembly (110) is integral with top (126) such that detaching upper section (120) from lower section (118) removes blade assembly (110) from within lower section (118). Other connection configurations between upper section (120) and lower section (118) will be apparent to those of ordinary skill in the art in view of the teachings herein.

While housing (116) has been described as having removable upper section (120) to permit insertion of tissue within lower section (118) of housing (116), other configurations for providing the ability to insert tissue within housing (116) will be apparent to those of ordinary skill in the art in view of the teachings herein (e.g., a selectively sealable side access window in sidewall (122) of housing (116), etc.). Housing (116) is constructed of a biocompatible material suitable for holding tissue particles. For instance, in some versions housing (116) is constructed of titanium, stainless steel, ceramic, or plastic. Other suitable materials for the construction of housing (116) will be apparent to those of ordinary skill in the art in view of the teachings herein. Other components of device (100) are contained within housing (116) as will be discussed further below.

Still referring to FIG. 2, fluid outlets (112) are spaced along the vertical sidewall (122) of housing (116). Fluid outlets (112) comprise open first ends (128) (refer to FIGS. 3-5) communicating with an interior (129) of housing (116), and open second ends (130) protruding from housing (116). Fluid outlets (112) define passageways (132) extending from open first ends (128) to open second ends (130). Fluid outlets (112) are selectively opened or closed depending on the procedure for which device (100) is being used. For example, fluid outlets (112) are closed during a tissue dicing procedure in some versions. Then at a desired point in the tissue particle separation procedure fluid outlets (112) are opened. In the illustrated version shown in FIG. 2, the opening and closing of fluid outlets (112) is accomplished using valves (114). While valves (114) are selectively opened and closed in accordance with signals from control module (104) in the present example (e.g., based on the operating mode of device (100), etc.), valves (114) may instead be configured for manual operation. For instance, valves (114) may comprise manually operable stopcocks in some versions. In some other versions, open second ends (130) of fluid outlets (112) are blocked using a stopper or other structure to selectively open and close fluid outlets (112). Other suitable structures and configurations for providing selective opening and closing of fluid outlets (112) will be apparent to those of ordinary skill in the art in view of the teachings herein.

The vertical spacing of fluid outlets (112) permits withdrawal of tissue particles having different particle size ranges. For instance, in some exemplary uses, housing (116) is filled with a fluid after a dicing procedure is complete, making a slurry of fluid and tissue particles. The slurry is then stirred, as discussed further below, creating a vortex within housing (116). This vortex causes separation of the slurry into a gradient having larger heavy tissue particles—which remain near the bottom of housing (116)—to a slurry having smaller light tissue particles—which move near the top of housing (116). Having fluid outlets (112) spaced vertically along housing (116) allows withdrawal of slurry having tissue of different particle size ranges. For instance, slurry with larger tissue particles is withdrawn from lower fluid outlet (134), slurry with medium-sized tissue particles is withdrawn from middle fluid outlet (136), and slurry with small tissue particles is withdrawn from upper fluid outlet (138). As will be discussed in greater detail below, various parameters may be controlled to achieve withdrawal of a slurry having a desired particle size from a given fluid outlet (134, 136, 138).

As mentioned above, valves (114) are connected with fluid outlets (112). Valves (114) are operable independently or jointly as mentioned above with respect to control module (104). While valves are controllable from control module (104), in some versions valves (114) may be manually controlled by a user instead. Valves (114) are of any suitable type configurable to selectively permit flow from fluid outlets (112) (e.g., ball valves, globe valves, gate valves, butterfly valves, etc.). Other suitable valve types will be apparent to those of ordinary skill in the art in view of the teachings herein.

Figure 3:
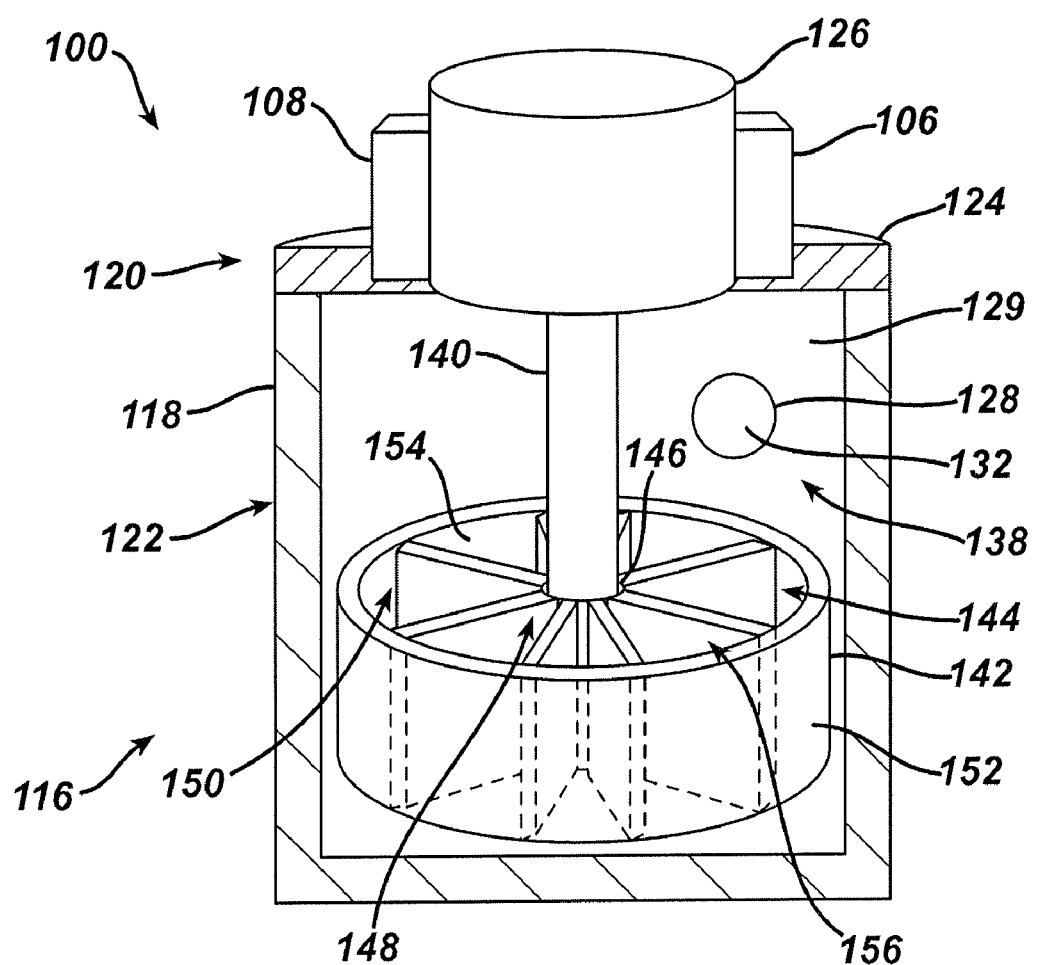
FIG. 3 depicts a perspective view of the device of FIG. 1, with the lower part of the housing shown in cross section, and the blade in a lowered position.
Figure 4:
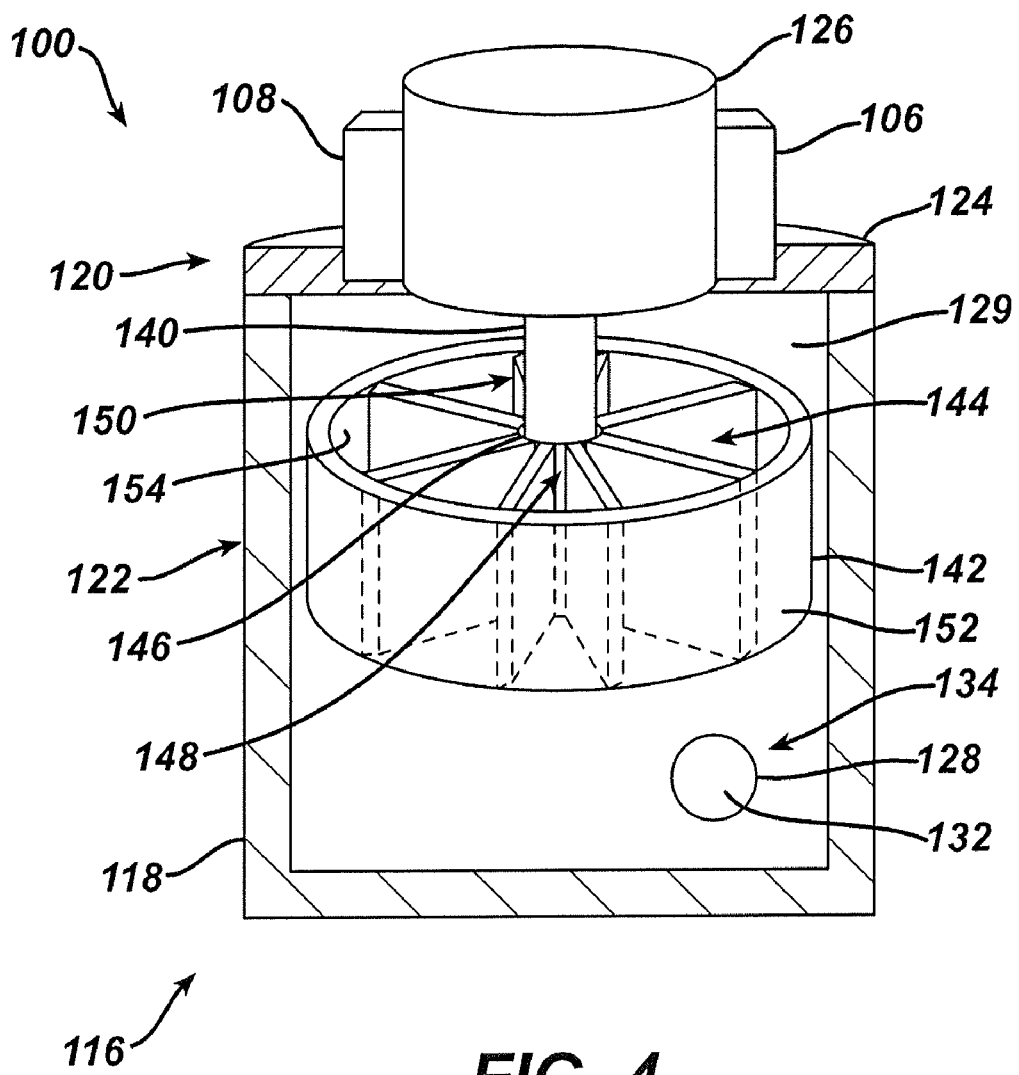
FIG. 4 depicts a perspective view of the device of FIG. 1, with the lower part of the housing shown in cross section, and the blade in a raised position.
Figure 5:
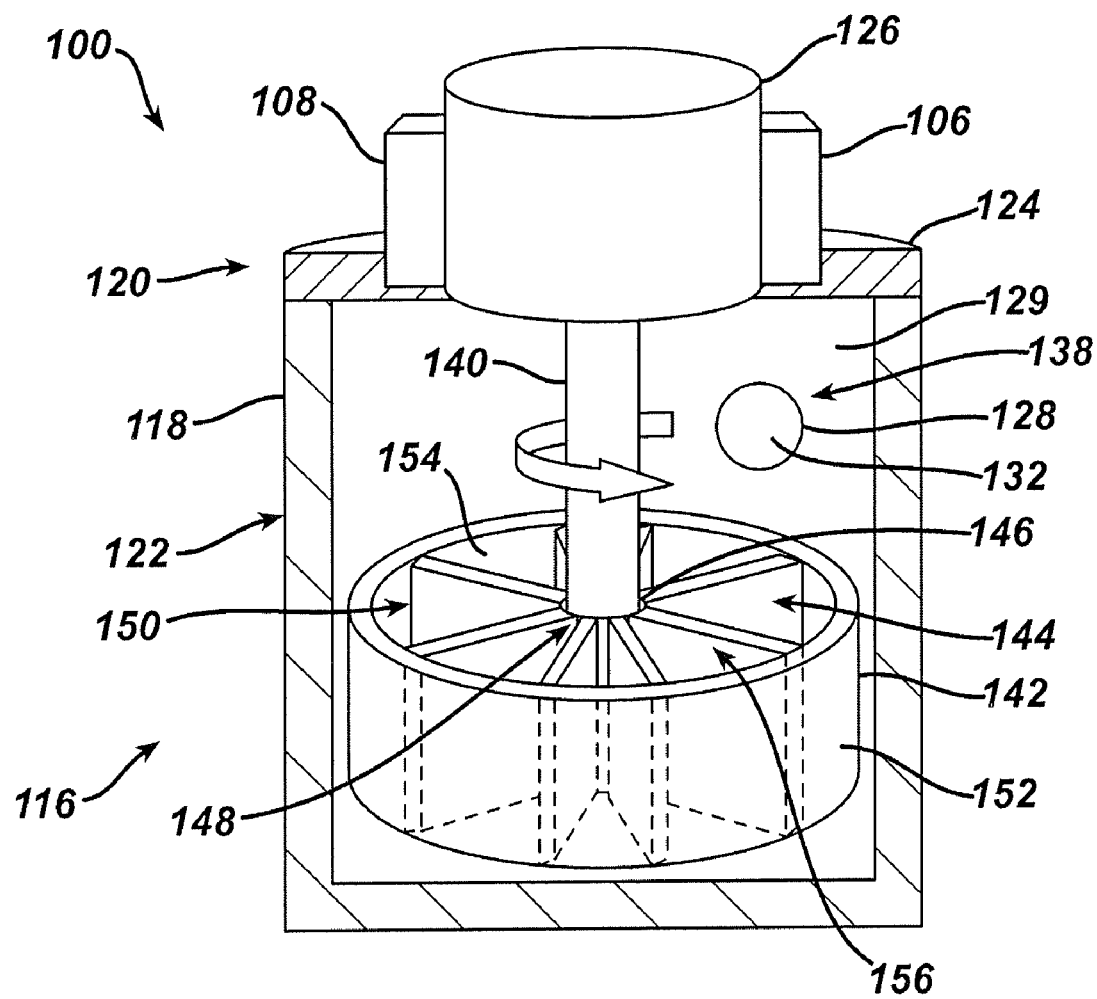
FIG. 5 depicts a perspective view of the device of FIG. 1, with the lower part of the housing shown in cross section, with the blade in a lowered position, and with the blade spinning.

Referring to FIGS. 3-5, lower section (118) of housing is shown in cross section, revealing more details of blade assembly (110). In the illustrated version shown in FIG. 3, blade assembly (110) is in a lowered position. Blade assembly (110) can be in this position initially, before tissue has been added to device (100), and then again after tissue has been added to device (100) and upper section (120) has been sealably joined with lower section (118) of housing (116).

Blade assembly (110) of the present example comprises shaft (140), outer blade (142), inner blades (144), and connector (146). As illustrated in FIG. 3, shaft (140) is associated with and extends from within top (126) of upper section (120) of housing (116) in a downward direction where it joins connector (146). Connector (146) has a cylindraceous shape in the illustrated versions of FIGS. 3-5, and each of a plurality of inner blades (144) connect with and extend radially outwardly from connector (146). Of course, in some versions connector (146) may be eliminated and inner blades (144) may be connected directly to shaft (140) or other components. In the illustrated version of FIG. 3, inner blades (144) have a rectangular shape with a first end (148) connecting to connector (146), and a second end (150) connecting with outer blade (142). Outer blade (142) has an outside surface (152) and inside surface (154). As shown, second ends (150) of each inner blade (144) connect with inside surface (154) of outer blade (142). With this configuration, inner blades (144), outer blade (142), and connector (146) define spaces (156) between pairs of inner blades (144). Thus as shown, blade assembly (110) provides for a circular wheel-and-spoke shape centered around shaft (140), presenting an outer diameter closely matching the inner diameter of housing (116). Of course, other suitable configurations for blade assembly (110) will be apparent to those of ordinary skill in the art in view of the teachings herein.

Referring to FIG. 4, blade assembly (110) is shown in a raised position. Blade assembly (110) assumes this position during the dicing operation. With tissue within housing (116), blade assembly (110) is reciprocated up and down to impart a dicing action to blade assembly (110). This reciprocating action is achieved by energizing and de-energizing solenoid (108). As mentioned above, solenoid (108) is configured with a resilient bias that maintains blade assembly (110) in the lowered position when solenoid (108) is not energized. When solenoid (108) is energized, the resilient bias is overcome and blade assembly (110) is moved to the raised position shown in FIG. 4. Of course, in other versions the configuration and operability of solenoid (108) could be reversed (e.g., with the resilient bias maintaining blade assembly (110) in the raised position and then energizing solenoid (108) moves blade assembly (110) to the lowered position). Furthermore, solenoid (108) may lack a resilient bias altogether in some versions.

In the illustrated version of FIG. 4, shaft (140) has a telescopic design such that when solenoid (108) is energized and the resilient bias overcome, concentric sections of shaft (140) telescope within one another to raise the other components of blade assembly (110) discussed above. In some other versions, shaft (140) is substantially rigid along its entire length such that it does not telescope. In some such versions, top (126) is configured to accommodate the top length of shaft (140) when shaft (140) is in a raised position. Alternatively, top (126) may include an opening configured to permit a portion of shaft (140) to protrude therethrough. In still other versions, shaft (140) itself does not reciprocate, and connector (146) is coupled with solenoid (108) and is operably configured to slide up and down along shaft (140) as solenoid (108) is energized and de-energized. Other suitable configurations for blade assembly (110) and its association with solenoid (108) for reciprocating blade assembly (110) will be apparent to those of ordinary skill in the art in view of the teachings herein.

During reciprocating cycles of blade assembly (110), motor (106) is also energized and de-energized to clock blade assembly (110). This clocking motion rotates blade assembly (110) slightly and incrementally from an initial rotational position to a new rotational position at each reciprocation stroke. Thus when blade assembly (110) reciprocates to dice the tissue, inner blades (144) have rotated slightly from their prior position to cause the tissue to be cut into smaller pieces. This clocking and reciprocating process is repeated until the tissue is diced to a desired degree. As mentioned above, control module (104) is operably configured to control motor (106) and solenoid (108) such that they operate in the desired fashion described above. In view of the teachings herein, those of ordinary skill in the art will understand how to configure control module (104) to achieve the described operative features of motor (106) and solenoid (108). Also, while the illustrated versions of FIGS. 3-5 describe blade assembly (110) as being clocked, in other versions the alignment of blade assembly (110) and the tissue may be altered by other means. By way of example only, in some versions device (100) may be fitted with a rotatable table for holding the tissue within housing (116) and motor (106) may clock the table to rotate the tissue. In still other versions, blade assembly (110) simply reciprocates and is not clocked or otherwise rotated. Other configurations and approaches for manipulating the tissue and blade assembly (110) orientation during the dicing procedure will be apparent to those of ordinary skill in the art in view of the teachings herein.

The desired degree of tissue dicing may be determined in a variety of ways. For example, dicing time and/or dicing cycles may be controlled to achieve a desired degree of tissue dicing. Also for example, visual inspection and/or other sampling and testing could be used to determine a desired degree of tissue dicing has been achieved. Other ways to control and monitor dicing degree will be apparent to those of ordinary skill in the art in view of the teachings herein. In the exemplary versions shown and described here, a target tissue particle size is between 200 and 500 microns. Of course the procedure may be altered to achieve other desired sized particles.

Referring now to FIG. 5, device (100) is shown with blade assembly (110) in the lowered position, and rotating in the direction indicated by the arrow. This is an exemplary configuration for use when performing the separation procedure after having diced the tissue. In the illustrated versions, dicing and separation of tissue particles occurs in the same device (100). Of course it will be understood that the dicing and separation procedures could be conducted in separate devices (e.g., by merely transferring the diced tissue particles from the dicing device to the separation device).

Prior to rotation of blade assembly (110) for the separation procedure, housing (116) of device (100) is filled with a fluid to create the slurry mentioned above. In some versions the fluid is saline. In other versions the fluid may be Ringer's solution, lactated Ringer's solution, Hartmann's solution, or another suitable fluid. It should also be understood that the fluid may comprise any of the medical fluid components referred to herein. To fill housing (116), upper section (120) may be removed temporarily and then replaced. In some versions, one of the fluid outlets (112) is opened and fluid is injected within housing (116). In some other versions, device (100) includes a port fitted with a one-way valve or septum for adding fluid to the interior (129) of housing (116). In such versions, the port may be located in sidewall (122), lid (124), top (126), or one of the fluid outlets (112) of device (100). The amount of fluid added to device (100) is controlled to achieve a desired slurry concentration having desired sized tissue particles. For example, the amount of fluid to add to achieve a desired concentration of a desired particle size can be generally calculated based on the known diced tissue mass or volume and customary particle size distribution after dicing (e.g., determined empirically), along with the known desired concentration and particle size of slurry for a particular use (e.g., fistula treatment, etc.). Various suitable methods for determining a preferable slurry concentration will be apparent to those of ordinary skill in the art in view of the teachings herein.

With housing (116) containing the desired amount of fluid, control module (104) is used to activate motor (106), which provides rotational energy to blade assembly (110). Motor (106) includes two operation modes—one mode is clocking for tissue dicing as discussed above, and the other mode is continuous rotation for tissue particle separation. In the illustrated version of FIG. 5, motor (106) is in the continuous rotation mode for tissue particle separation.

During the separation process, blade assembly (110) remains biased to the lowered position as solenoid (108) is not energized. With blade assembly (110) rotating, a vortex is created within housing (116) such that the tissue particles separate by particle size. The larger heavy particles remain near the bottom of housing (116), the medium-size particles travel toward the middle region of housing (116), and the smaller lighter particles travel toward the upper region of housing (116). Fluid outlets (112) are available at various vertical positions along housing (116) to withdrawal slurry at the different points as discussed above. Control module (104) is operable to vary the motor speed such that the RPM of blade assembly (110) is controllable so that slurry having the desired particle size can be withdrawn from the desired fluid outlet (112). In the illustrated versions of FIGS. 2-5, slurry having tissue particles in the range of 200-500 microns is withdrawn from middle fluid outlet (136). Slurry having the larger heavier particles is withdrawn from lower fluid outlet (134), and may be recycled for further dicing in subsequent procedures. Slurry having the smaller lighter particles is withdrawn from upper fluid outlet (138) and is discarded as waste or set aside for another use.

Once the desired slurry has been obtained, it may be used in a treatment application (e.g., fistula treatment) by delivering the slurry in a desired and/or efficacious amount via a treatment delivery system, examples of which are described in the references cited herein. In some versions, before the desired slurry is used in a treatment application, the slurry may be further concentrated or diluted depending on the application for which the tissue particles will be used. In some versions, the tissue particles may be separated from the fluid and mixed with other treatment components, or other treatment components added to the existing slurry. It should be understood that the tissue particles may be mixed with any of the medical fluid components described herein. Other numerous applications for using the tissue particles will be apparent to those of ordinary skill in the art in view of the teachings herein.

Referring to FIGS. 3-5, while numerous features of device (100) have been shown and discussed, it will be appreciated that several features not discussed in great detail will be apparent to those of ordinary skill in the art in view of the teachings herein. For example, the association of shaft (140) with motor (106) and solenoid (108) has been described; however, further specifics regarding exemplary connection modes between shaft (140), motor (106), and solenoid (108) will be apparent to those of ordinary skill in the art in view of the teachings herein. Also for example, further specifics regarding exemplary logic for control module (104) will be apparent to those of ordinary skill in the art in view of the teachings herein. While shaft (140) extends downwardly from top (126) in the present example, shaft (140) may alternatively extend upwardly from the bottom of housing (116). Likewise, while motor (106) and solenoid (108) are located in top (126) in the present example, motor (106) and/or solenoid (108) may alternatively be located at the bottom of housing (116). Still other suitable components, features, configurations, and operabilities that may be provided in or by device (100) will be apparent to those of ordinary skill in the art in view of the teachings herein.

III. Exemplary Method and Device for Fistula Plug Manufacture

FIGS. 6-10 show an exemplary method and device for making a fistula plug for use in surgery to treat a fistula or other type of anatomical defect, etc. For instance, the plug may be sized and configured for delivery into a variety of fistula tracts. As described in more detail below, in some versions, slurry obtained from the above described device (100) and method may be used in conjunction with a fistula plug made using the below described device and method. In particular, the plug generally comprises a scaffold material (300) formed into a narrow cylindrical shape that is configured for insertion into a fistula with a cell matrix. Scaffold material (300) may comprise a biocompatible material that may be formed from a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, polyhydroxybutyrate (PHB), poly(hyaluronic acid), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.), and/or any other suitable material or combination of materials. It should also be understood that scaffold material (300) may include any one or more of the various medical fluid components referred to herein. Other suitable materials will be apparent to those of ordinary skill in the art in view of the teachings herein.

As will be described in greater detail below, a plug formed of scaffold material (300) may be inserted into a fistula by a catheter (326), and may be flushed with a cell matrix to therapeutically address the fistula. Such a cell matrix may be formed at least in part by tissue that was harvested from the same patient that has the fistula (and/or tissue harvested from some other source or sources). For instance, at least some of the cells in the cell matrix may be isolated or derived in part from such harvested tissue. The cells may include, for example, genetically engineered cells, precursor cells, progenitor cells, precursor cells, stem cells, bone marrow cells, umbilical cord blood cells, angioblasts, endothelial cells, osteoblasts, smooth muscle cells, kidney cells, fibroblasts, myofibroblasts, cardiovascular cells, neural cells, neural precursor cells, amniotic cells and post-partum placental cells, any other type of cells referred to herein, and/or any other suitable types of cells, including combinations of different kinds of cells. The harvested tissue may have been minced using device (100) and/or may have been processed in any other suitable fashion before being introduced to scaffold material (300). While the cell matrix is introduced to a plug formed by scaffold material (300) after the plug has been inserted in a fistula or as the plug is being inserted in a fistula in the present example, it should be understood that the cell matrix may alternatively be introduced to scaffold material (300) before or during the process in which scaffold material (300) is formed into a plug or at any other suitable time.

Figure 6:
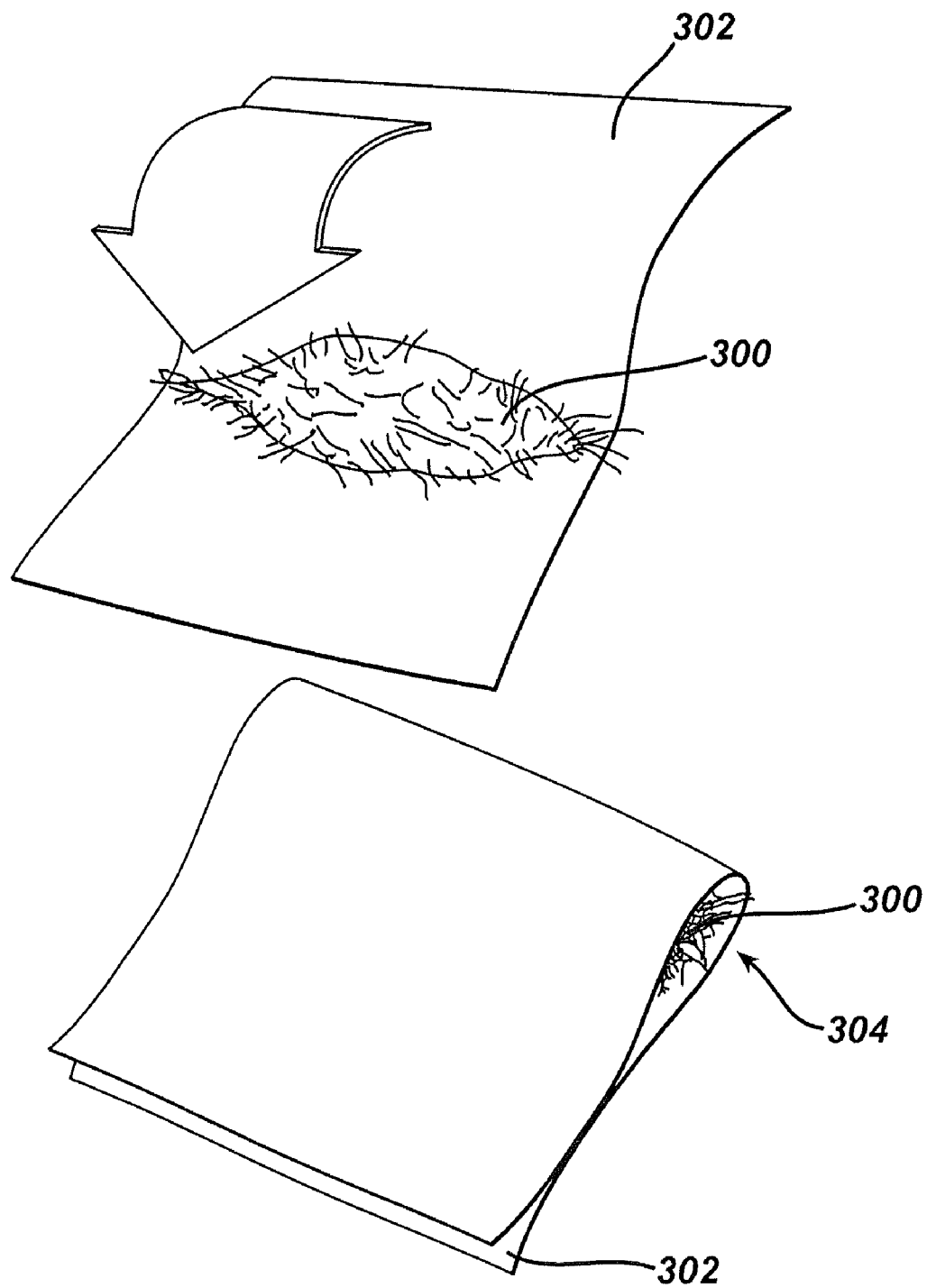
FIG. 6 depicts a first series view, in perspective, of an exemplary fistula plug assembly device.

The fistula plug preparation system of this example comprises a sheet (302), a slotted plate (308), a tube (318), a loading rod (330), and a catheter (326). Sheet (302) generally comprises a thin foldable sheet operable to receive scaffold material (300). Sheet (302) may be formed at least in part of a material or materials such as silicone, ultra high molecular weight polyethylene, polytetrafluoroethylene (PTFE), etc., that is configured to prevent scaffold material (300) from sticking to sheet (302), even if sheet (302) is folded over itself with scaffold material (300) contained therein. Still yet other suitable materials for sheet (302) will be apparent to those of ordinary skill in the art in view of the teachings herein. Sheet (302) of the present example is configured to transition from a flat position to a folded position as shown in FIG. 6. However, any suitable position for sheet (302) may be used to enclose scaffold material (300). As shown in FIG. 6, a scaffold material (300) is placed on a sheet (302). In particular, scaffold material (300) is placed on sheet (302) so that scaffold material (300) is generally centered lengthwise on sheet (302) and extends somewhat in equal amounts across the width of sheet (302). Once scaffold material (300) is placed on sheet (302), sheet (302) is then folded widthwise in the direction of the arrow shown in FIG. 6. In this folded configuration, sheet (302) forms a pocket (304) and pocket (304) contains scaffold material (300). Furthermore, in this configuration sheet (302) generally begins to form scaffold material (300) into a rod-like shape.

Slotted plate (308) of the present example comprises a generally flat and rectangular plate. However, it should be understood that slotted plate (308) may have any other suitable shape, configuration, or size. Slotted plate (308) defines a slot (306) extending through slotted plate (308). Slot (306) of plate (308) is configured such that it has an open end (314) and closed end (316). Slot (306) thus extends along almost the entire length of slotted plate (308) such that a portion of slotted plate (308) still connects what would otherwise be two separate portions of slotted plate (308). Plate (308) may be constructed of stainless steel, plastic, ceramic, and/or other suitable materials. In view of the teachings herein, other suitable materials for plate (308) will be apparent to those of ordinary skill in the art.

Figure 7:
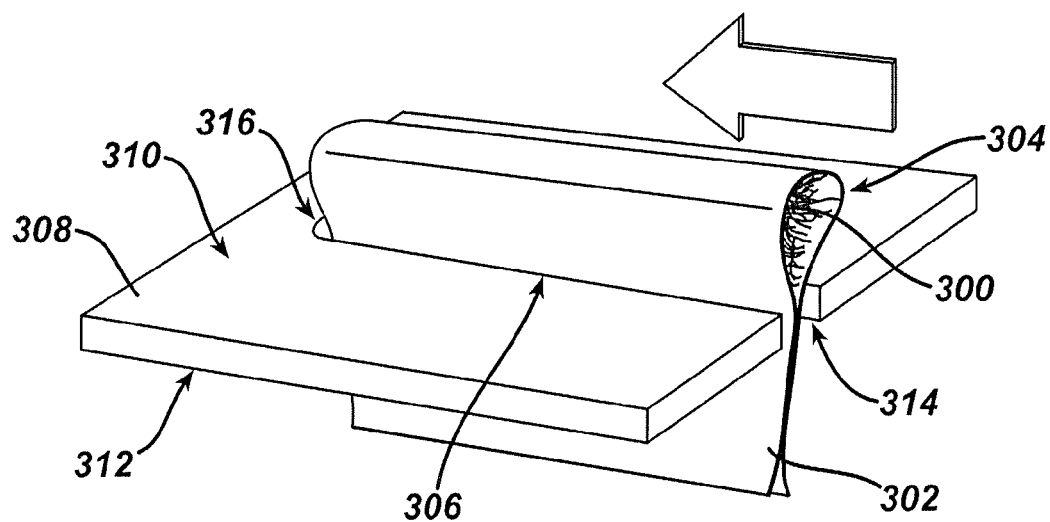
FIG. 7 depicts a second series view, in perspective, of the exemplary fistula plug assembly device of FIG. 6.

As shown in FIG. 7, sheet (302), in its folded position and containing scaffold material (300), is placed within slot (306) of plate (308). As shown, when placed within slot (306), pocket (304) containing scaffold material (300) is located on top side (310) of plate (308) and the ends of sheet (302) extend from the bottom side (312) of plate (308). Thus to insert sheet (302) within slot (306), sheet (302) may be slid in from the side as shown by the arrow in FIG. 7 until sheet (302) abuts closed end (316). Slot (306) is sufficiently narrow so as to prevent scaffold material (300) from inadvertently falling out of sheet (302) thought slot (306). At this stage, sheet (302) may be pulled downwardly relative to slotted plate (308). It should be understood that such pulling may allow sheet (302) to compress scaffold material (300) by bearing against slotted plate (308). In addition or in the alternative, opposite ends of sheet (302) may be alternatingly pulled down in a rocking fashion to roll scaffold material (302) within sheet (302).

Figure 8:
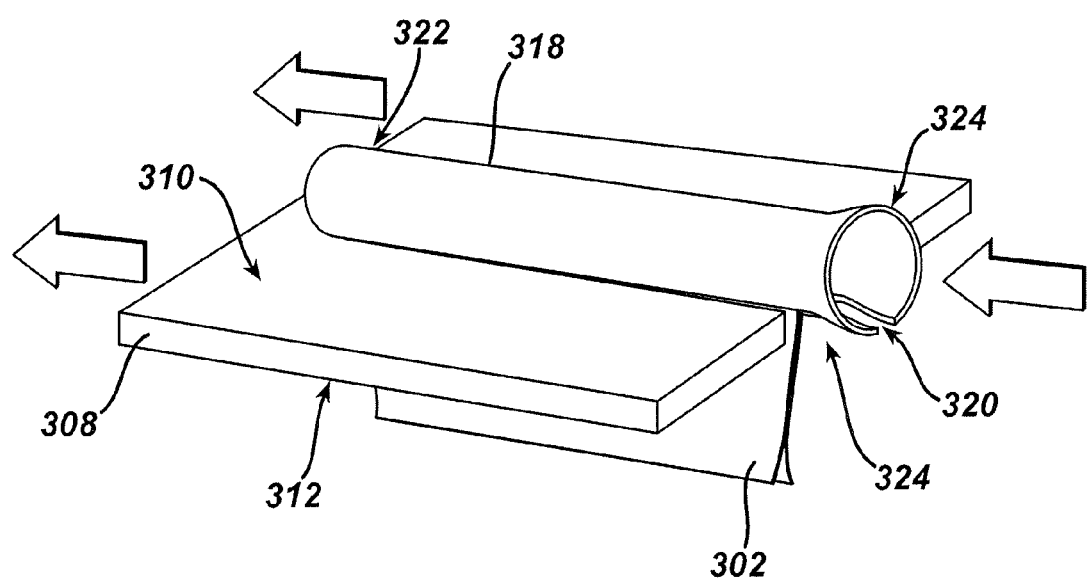
FIG. 8 depicts a third series view, in perspective, of the exemplary fistula plug assembly device of FIG. 6.

As shown in FIG. 8, tube (318) of the present example comprises a cylindrical tube having a flared end (324). While sheet (302) is substantially flexible in the present example, tube (318) is substantially rigid (e.g., formed of steel, rigid plastic, etc.) in the present example Tube (318) further comprises a slot (320) extending along the full length of tube (318). Slot (320) is configured to allow sheet (302) containing scaffold material (300) to fit within tube (318) such that at least a portion of sheet (302) extends though slot (320) of tube (318) in addition to extending through slot (306) of slotted plate (308). Flared end (324) of tube (318) is configured to allow easy insertion of sheet (302) containing scaffold material (300) into tube (318). Furthermore, the inner diameter of tube (318) may be smaller than the outer diameter of sheet (302) containing scaffold material (300), such that once tube (318) is placed over sheet (302) containing scaffold material (300), sheet (302) containing scaffold material (300) is compressed to form scaffold material into a generally cylindrical plug shape. Of course, tube (318) may be any other suitable shape, and may be configured to form scaffold material (300) into any other suitable shape. Although tube (318) is substantially rigid, in some versions, tube (318) is also resilient and/or flexible to some degree such that slit (320) is biased to a closed position or nearly closed position when tube (318) is at rest, and slit (322) can be opened to some degree when tube (318) is flexed in an outward direction from slit (322). Thus, in such versions when applying tube (318) over sheet (302), force is applied to tube (318) so that slit (322) opens such that tube (318) can be easily slid over sheet (302) from the side as shown by the right-side arrow in FIG. 8. Still in other versions, tube (318) may be sufficiently resilient and/or flexible such that slit (322) may be opened wide enough to fit over pocket (304) so that tube (318) may be positioned over pocket (304) of sheet (302) from the top instead of being slid in from the side.

After tube (318) has been positioned around the portion of sheet (302) forming pocket (304) as shown in FIG. 8, plate (308) is removed by sliding plate (308) away from the tube (318) and sheet (302) combination as shown by the left-side arrow of FIG. 8. Other configurations for tube (318) and techniques for using tube (318) with sheet (302) and plate (308) will be apparent to those of ordinary skill in the art in view of the teachings herein.

Figure 9:
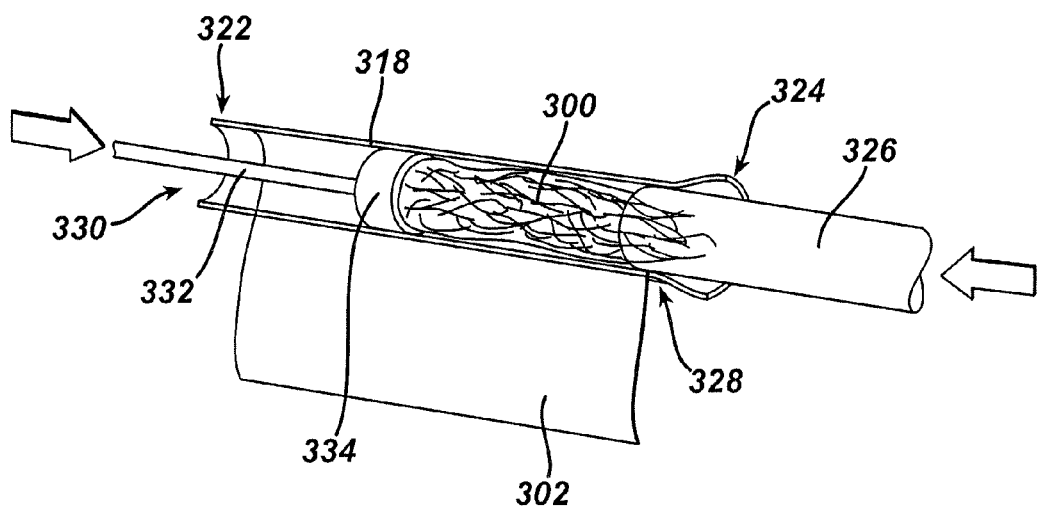
FIG. 9 depicts a fourth series view, in perspective, of the exemplary fistula plug assembly device of FIG. 6, shown with the tube in cross section.
Figure 10:
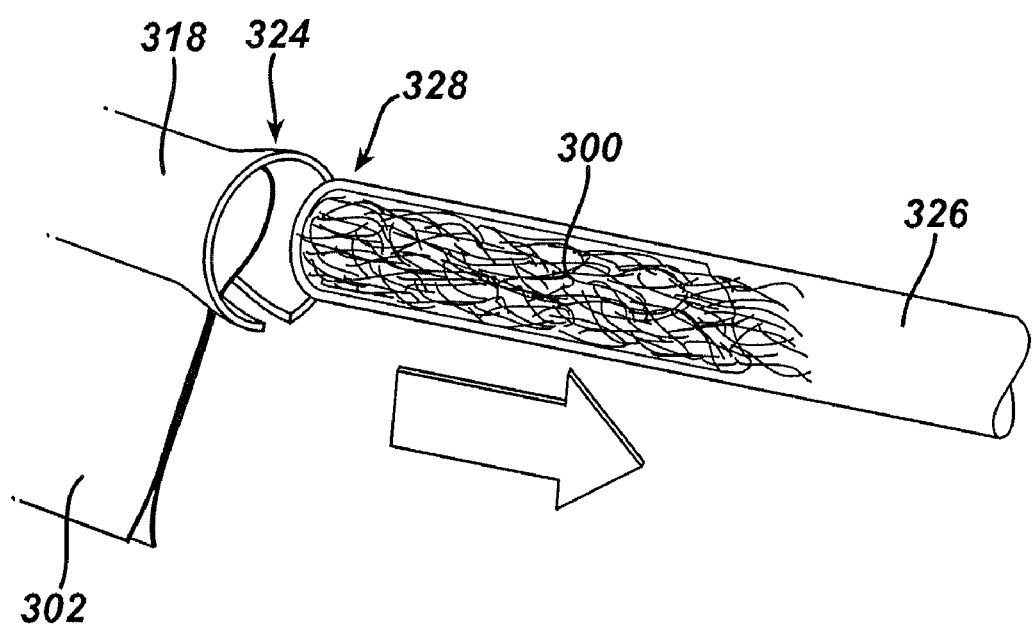
FIG. 10 depicts a fifth series view, in perspective, of the exemplary fistula plug assembly device of FIG. 6.

Referring to FIGS. 9 and 10, scaffold material (300) is now ready for installation within a delivery device (e.g., a catheter (326) as shown in the illustrated versions of FIGS. 9 and 10). Catheter (326) of the present example has a generally cylindrical shape, though it should be understood that any other suitable shape may be used. Catheter (326) may be positioned at flared end (324) of forming device (406) for receipt of scaffold material (300). In particular, catheter (326) is partially inserted within tube (318) as shown by the right-side arrow of FIG. 9. The outwardly flared configuration of flared end (324) of tube (318) may guide and facilitate such insertion. In the illustrated version shown in FIG. 9, catheter (326) has a diameter that is smaller than the diameter of flared end (324) of tube (318), but larger than the diameter of the majority of tube (318). This configuration of diameters provides that catheter (326) is not over-inserted within tube (318) and that the first end (328) of catheter (326) abuts the interior of tube (318) creating a seal between tube (318) and catheter (326).

With catheter (326) inserted within tube (318) at flared end (324) of tube (318), loading rod (330) is inserted within tube (318) at first end (322) of tube (318) as shown by the left-side arrow of FIG. 9. Loading rod (330) comprises a shaft (332) and pusher (334). Pusher (334) is configured with an outer diameter that substantially matches the inner diameter of first end (322) and the majority of tube (318) such that pusher (334) is operable to slide within tube (318). As loading rod (330) is advanced within tube (318), pusher (334) drives plug (330) into catheter (326). Once loading rod (330) has reached first end (328) of catheter (326), or when catheter (326) contains a sufficient amount of scaffold material (300), catheter (326) is removed from tube (318) as shown by the arrow in FIG. 10.

With catheter (326) containing scaffold material (300) and being withdrawn from tube (318), this device can later be used in a treatment procedure. In some versions, catheter (326) containing scaffold material (300) may be stored for later use. In an exemplary fistula treatment, catheter (326), containing scaffold material (300), is inserted into the tract of a fistula, such that scaffold material (300) may be ejected as a plug into the fistula. At an end of catheter (326) opposite first end (328) containing scaffold material (300), catheter (326) is connected with a tissue cell matrix for injecting within the fistula. In one exemplary version, the tissue cell matrix is a slurry of fluid and tissue particles as described above. Catheter (326) is then withdrawn from the fistula while flushing the fistula with the tissue cell matrix such that the tissue cell matrix forces scaffold material (300) from catheter (326) into the fistula site. The impregnated scaffold material (300) may thus be deployed within the fistula in a manner similar to that by which a self-expanding stent is deployed. As scaffold material (300) contacts the tissue cell matrix, scaffold material (300) absorbs and expands thus filling all or a portion of the fistula and distributing the tissue cell matrix. The therapeutic nature of the tissue cell matrix contributes to tissue healing in and around the fistula and ultimately scaffold material (300) is absorbed in the surrounding tissue by hydrolysis.

Of course, scaffold material (300) may alternatively be deployed in any other suitable fashion. Still other suitable features, components, configurations, functionalities, and operabilities that may be provided by a fistula plug preparation system will be apparent to those of ordinary skill in the art in view of the teachings herein. Similarly, various other suitable ways in which a fistula plug preparation system such as one described herein may be used will be apparent to those of ordinary skill in the art in view of the teachings herein.

IV. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by those of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for dicing and separating tissue, wherein the device comprises:
    (a) a housing defining an interior space, wherein the interior space has a cross sectional profile, wherein the housing comprises an opening providing access to the interior space, wherein the housing comprises at least one outlet extending from the housing and providing a passageway to the interior space of the housing;
    (b) a blade assembly comprising a blade portion configured to complement the cross sectional profile of the interior space of the housing;
    (c) a linear actuating member, wherein the actuating member is operably configured to linearly reciprocate the blade assembly; and
    (d) a rotary actuating member having a first mode and a second mode, wherein in the first mode the rotary actuating member is operably configured to clock the blade assembly during reciprocation of the blade assembly, wherein in the second mode the rotary actuating member is operably configured to continuously rotate the blade assembly separate from the reciprocation of the blade assembly.

2. The device of claim 1, wherein the housing comprises a lower section and an upper section, wherein the upper section is selectively sealable to the lower section.

3. The device of claim 2, wherein the blade assembly is secured to the upper section and removable from the lower section when the upper section is removed from the lower section.

4. The device of claim 1, wherein the rotary actuating member comprises a motor.

5. The device of claim 1, wherein the at least one outlet includes a valve.

6. The device of claim 1, wherein the at least one outlet comprises three outlets, wherein the outlets are spaced vertically along the housing.

7. The device of claim 6, wherein the three outlets each include a respective valve.

8. The device of claim 1, wherein the linear actuating member is biased to maintain the blade assembly in a lowered position.

9. The device of claim 8, wherein the linear actuating member comprises a solenoid, wherein the solenoid is operably configured to raise the blade assembly to an upper position when the solenoid is energized.

10. The device of claim 1, further comprising a control module, wherein the control module is operable to control rotation and reciprocation of the blade assembly through control of the linear actuating member and the rotary actuating member.

11. The device of claim 10, wherein the control module is operable to selectively adjust the speed of rotation and reciprocation of the blade assembly.

12. A device for dicing and separating tissue, wherein the device comprises:
    (a) a housing defining an interior space, wherein the housing comprises an opening providing access to the interior space, wherein the housing comprises at least one outlet extending from the housing and providing a passageway to the interior space of the housing;
    (b) a blade assembly comprising at least a pair of blades defining an aperture therebetween, wherein the blade assembly is integral with at least a portion of the housing;

(c) a linear actuator, wherein the linear actuator is operably configured to reciprocate the blade assembly within the interior space;

(d) a rotary actuator, wherein the rotary actuator is operably configured to continuously rotate the blade assembly separate from the reciprocation of the blade assembly; and (e) a control module, wherein the control module is operable to control rotation and reciprocation of the blade assembly through control of the linear actuator and the rotary actuator.

13. The device of claim 12, wherein the blade assembly comprises a shaft and a blade portion.

14. The device of claim 13, wherein the blade portion comprises an inner blade portion and an outer blade portion, wherein the inner blade portion comprises a plurality of individual inner blades, each inner blade having a respective first end and second end, wherein the first end of each inner blade is associated with the shaft, wherein the second end of each inner blade is coupled with the outer blade portion.

15. The device of claim 14, wherein the blade assembly has a wheel-and-spoke-configuration, such that the plurality of individual inner blades extend radially outwardly relative to the shaft.

16. The device of claim 13, wherein the shaft is telescopic.

17. The device of claim 13, wherein the blade portion is operable to reciprocate longitudinally along the shaft.

18. The device of claim 12, further comprising a power source integral with the housing.

19. A method of processing tissue in a tissue processing device, wherein the tissue processing device comprises a blade member, a plurality of outlet ports, and an interior space, wherein each outlet port is associated with a corresponding tissue particle size range, the method comprising:

(a) depositing one or more tissue specimens in the interior space of the tissue processing device;

(b) reciprocating the blade member linearly within the interior space of the tissue processing device to mince the one or more tissue specimens;

(c) introducing a fluid medium to the interior space of the tissue processing device with the minced tissue to provide a fluid-tissue mixture;

(d) inducing a vortex within the interior space of the tissue processing device, wherein the vortex stirs the fluid-tissue mixture and lifts minced tissue particles in the fluid-tissue mixture, wherein the minced tissue particles are lifted to respective vertical positions corresponding to sizes of the minced tissue particles; and (e) receiving minced tissue through the plurality of outlet ports, wherein each outlet port receives minced tissue particles having sizes within the tissue particle size range associated with the corresponding outlet port, wherein the minced tissue is communicated to the outlet ports based on the vortex induced within the interior space of the tissue processing device.

20. The method of claim 19, wherein the act of inducing a vortex within the interior space of the tissue processing device comprises rotating the blade member within the interior space of the tissue processing device.

* * * * *